US007534908B2

(12) United States Patent
Sorger et al.

(10) Patent No.: US 7,534,908 B2
(45) Date of Patent: May 19, 2009

(54) METHOD FOR THE PRODUCTION OF OPTICALLY ACTIVE 3-ALKYLCARBOXYLIC ACIDS AND THE INTERMEDIATE PRODUCTS THEREOF

(75) Inventors: Klas Sorger, München (DE); Jürgen Stohrer, Pullach (DE)

(73) Assignee: Wacker Chemie AG, Munich (DE)

( * ) Notice: Subject to any disclaimer, the term of this patent is extended or adjusted under 35 U.S.C. 154(b) by 80 days.

(21) Appl. No.: 11/569,452

(22) PCT Filed: May 12, 2005

(86) PCT No.: PCT/EP2005/052163

§ 371 (c)(1),
(2), (4) Date: Mar. 29, 2007

(87) PCT Pub. No.: WO2005/115955

PCT Pub. Date: Dec. 8, 2005

(65) Prior Publication Data

US 2007/0225519 A1    Sep. 27, 2007

(30) Foreign Application Priority Data

May 27, 2004   (DE)   ................. 10 2004 025 901

(51) Int. Cl.
*C07C 51/38* (2006.01)
*C07C 53/126* (2006.01)
*C07C 55/02* (2006.01)
*C07B 53/00* (2006.01)

(52) U.S. Cl. ........................................... 560/29
(58) Field of Classification Search ............... None
See application file for complete search history.

(56) References Cited

U.S. PATENT DOCUMENTS 5,245,079 A    9/1993   Murtiashaw

FOREIGN PATENT DOCUMENTS

EP    0 684 240 B1    8/2000

JP    3-95138    4/1991
WO    WO-93/22269    11/1993

OTHER PUBLICATIONS

Marshall et al. Journal of Organic Chemistry, 1966, 31(9), 2933-2941.*
Patent abstract corresponding to JP 3-95138.
Cason et al., Coad et al., Branched-Chain Fatty Acids. XVI. Synthesis of the Optical Isomers of 15-Methyloctadecanoic Acid, J. Am. Chem. Soc., 1950, vol. 72, pp. 4695-4697.
Rosen et al., Daussmann et al., Stohrer et al., Bioreduction forms optically active 3-hydroxyesters, Speciality Chemicals Magazine, 2004, pp. 39-40.
Sato et al., Otera et al., CsF in Organic Synthesis. Malonic Ester Synthesis Revisited for Stereoselective Carbon-Carbon Bond Formation, J. Org. Chem., 1995, pp. 2627-2629.
Bates et al., Devi et al., Acylation-Cyclization of Allenes Using Acyltetracarbonylcobalt Complexes, Tetrahedron Letters, 1995, pp. 509-512, vol. 36, No. 4.
Larchevêque et al., Petit et al., An Efficient Synthesis of Optically Active 2-Alkylsuccinate Monoesters, Synthesis, 1991, pp. 162-164.
Uenishi et al., Hamada et al., Chem. Pharm. Bull., 2002, pp. 697-700, vol. 50, No. 5.
Berens et al., Scharf et al., Eine neue Synthese von (S)-beta-methyl-gamma-butyrolacton und (S)-4-Benzyloxy-3-methylbutansäure, Synthesis, 1991, pp. 832-834.
Brown et al., Macintyre et al., J. Chem. Soc. Perkin Trans. II, 1985, pp. 961-970.

\* cited by examiner

*Primary Examiner*—Daniel M Sullivan
*Assistant Examiner*—Yevegeny Valenrod
(74) *Attorney, Agent, or Firm*—Brooks Kushman P.C.

(57) ABSTRACT

An enantioselective method for producing optically active 3-alkyl carboxylic acids comprises transforming an optically active secondary alcohol into an optically active, activated compound by introducing a leaving group; reacting the activated compound with a malonic acid derivative to obtain an optically active, alkylated malonic acid compound, the reaction taking place exclusively in ether and/or carboxylic acid ester solvents and one or more aprotic polar solvents or alcohols as a cosolvent in a maximum proportion of 30 volume percent of total solvent, wherein the added cosolvent is not hexamethyl phosphoric acid triamide; the malonic acid compound is hydrolyzed if necessary to obtain the corresponding acid; and the corresponding acid is decarboxylated.

17 Claims, No Drawings

METHOD FOR THE PRODUCTION OF OPTICALLY ACTIVE 3-ALKYLCARBOXYLIC ACIDS AND THE INTERMEDIATE PRODUCTS THEREOF

CROSS-REFERENCE TO RELATED APPLICATION

This application is the U.S. national phase of PCT Appln. No. PCT/EP2005/052163 filed May 12, 2005, which claims priority to German application 10 2004 025 901.1 filed May 27, 2004.

BACKGROUND OF THE INVENTION

1. Field of the Invention

The invention relates to a process for preparing optically active 3-alkylcarboxylic acids. Optically active 3-alkylcarboxylic acids are important synthesis units for the preparation of active pharmaceutical ingredients. For example (R)-3-methylheptanoic acid and (R)-3-methylhexanoic acid find use as constituents and/or synthesis units of active ingredients for immune regulation.

2. Description of the Related Art

U.S. Pat. No. 5,245,079 discloses a process in which (R)-3-methylheptanoic acid and (R)-3-ethylheptanoic acid are prepared in a multistage synthesis sequence starting from racemic trans-4-hexen-3-ol and trans-4-hepten-3-ol. In this process, an optical resolution (Sharpless reaction) takes place in the first synthesis step. The yield of this step is firstly restricted to 50% of theory, and several reaction steps of the process secondly require reactions at temperatures of <−60° C., which makes the process uneconomical especially for use on an industrial scale.

JP 03095138 and WO 9322269 describe optical resolution processes for preparing (R)-3-methylheptanoic acid and (S)-3-methylheptanoic acid by crystallization with the aid of 1-phenylethylamine and 1-phenylpropylamine as chiral assistants. In the two processes, the optically active carboxylic acids are obtained in sufficient enantiomeric excess of >97% ee only after several successive crystallizations and recrystallizations. The low yields of up to <15% of theory and the high process complexity do not meet the requirements for an economically viable process on the industrial scale.

U. Berens, H.-D. Scharf, Synthesis, 1991, p. 832 discloses the preparation of (S)-4-benzyloxy-3-methyl-butanoic acid. In this preparation, (S)-1-benzyloxypropan-2-ol is activated by tosylation, di-tert-butyl malonate is alkylated with the tosylate in polar aprotic dimethylformamide with inversion, and the alkylated malonic ester is hydrolyzed and decarboxylated to give (S)-4-benzyloxy-3-methylbutanoic acid. The reaction of the open-chain secondary toluene-sulfonate of (S)-1-benzyloxypropan-2-ol with the potassium salt of di-tert-butyl malonate in dimethylformamide proceeds, however, with partial racemization and only 65% chemical yield. The overall yield over all stages is only 45%.

None of the processes known from the prior art affords optically active 3-alkylcarboxylic acids in simultaneously high chemical and optical yields under conditions which are realizable on the industrial scale and/or of economic interest.

SUMMARY OF THE INVENTION

It is thus an object of the invention to provide an alternative process for preparing optically active 3-alkylcarboxylic acids. The object is achieved by a process which proceeds from an inexpensive, enantiomerically pure secondary alcohol reactant available on the industrial scale onto which is introduced a leaving group, and which is then reacted with a malonic acid derivative to form an optically active alkylated malonic acid compound, during the course of which a completely stereoselective inversion without racemization occurs, simultaneously with high yields.

DETAILED DESCRIPTION OF THE PREFERRED EMBODIMENTS

The invention provides an enantioselective process for preparing optically active 3-alkylcarboxylic acids, comprising the following steps:

A) conversion of an optically active secondary alcohol (II) to an optically active, activated compound (III) by introducing a leaving group, B) reacting the activated compound with a malonic acid derivative to give an optically active, alkylated malonic acid compound (IV), the reaction being effected exclusively in the presence of one or more solvents selected from the class of the ethers or of the carboxylic esters, one or more aprotic polar solvents or alcohols optionally being added as a cosolvent, this addition being a maximum of 30% of the total volume of solvent, C) optionally hydrolyzing to the corresponding acid (V) and D) finally decarboxylating the acid (V) to give the optically active 3-alkylcarboxylic acid as the product.

An essential feature of the inventive synthesis sequence is the fact that the reaction in step B) is effected by the selection of a suitable class of solvents or solvent mixtures which simultaneously provide virtually complete stereoselective inversion and very high yields.

The solvent is selected exclusively from one or more solvents selected from the class of the ethers or of the carboxylic esters. Optionally, one or more aprotic polar solvents or alcohols can be added as cosolvents to the ether or carboxylic ester solvent(s), where the proportion of the aprotic polar solvent(s) or alcohol(s) should not exceed 30% of the total volume of solvent with the proviso that the optionally added cosolvent is not hexamethylphosphoramide.

More particularly, the invention provides a process for preparing optically active 3-alkylcarboxylic acids of the general formula (Ia) or (Ib)

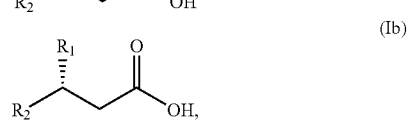

where $R^1$ and $R^2$ are each independently a linear or branched, saturated or unsaturated, cyclic or cyclic group-containing $C_1$-$C_{15}$ hydrocarbon radical which is optionally substituted by Q, wherein Q is selected from the group comprising halogen, amino, amido, phthalimido, hydroxyl, cyano, nitro, alkoxy, aryloxy, aralkyloxy, alkylthio, acyl, silyl, silyloxy, aryl, heteroaryl, comprising the following steps:

A) converting a compound of the general formula (IIa) or (IIb)

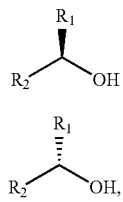
(IIa)

(IIb)

to activated compounds of the general formula (IIIa) or (IIIb)

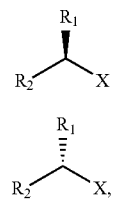
(IIIa)

(IIIb)

where

X is selected from the group comprising halogen, OSO$_2$R, OSO$_2$OR or OCOR and R is a linear or branched, saturated or unsaturated, cyclic or cyclic group-containing C$_1$-C$_{15}$ hydrocarbon radical which is optionally substituted by Q, B) reacting the compounds of the general formula (IIIa) or (IIIb) obtained in step A) with a malonic acid derivative to obtain compounds of the general formula (IVa) or (IVb), the reaction being effected exclusively in the presence of one or more solvents from the class of the ethers or of the carboxylic esters, one or more aprotic polar solvents or alcohols optionally being added as a cosolvent, this addition being a maximum of 30% of the total volume of solvent, and

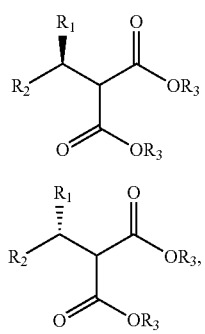
(IVa)

(IVb)

where

R$^3$ in the general formula (IVa) or (IVb) is in each case independently hydrogen or a linear or branched, saturated or unsaturated, cyclic or cyclic group-containing C$_1$-C$_{15}$ hydrocarbon radical or is a C$_1$-C$_{20}$ trialkyl- or C$_1$-C$_{20}$ triarylsilyl radical, C) optionally hydrolyzing the compounds of the general formula (IVa) or (IVb) obtained in step B) to obtain dicarboxylic acids of the general formula (Va) or (Vb)

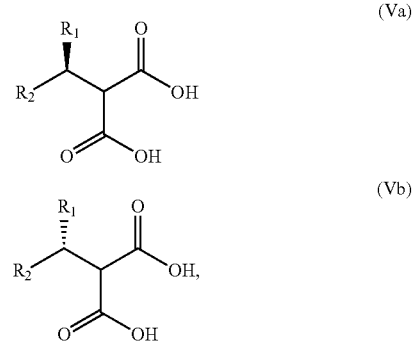
(Va)

(Vb)

D) and finally decarboxylating the dicarboxylic acid of the general formula (Va) or (Vb) obtained in step C).

Thus, it is possible by the process according to the invention to obtain, in particular, (R)-3-methylhexanoic acid starting from (S)-2-pentanol according to the following reaction scheme:

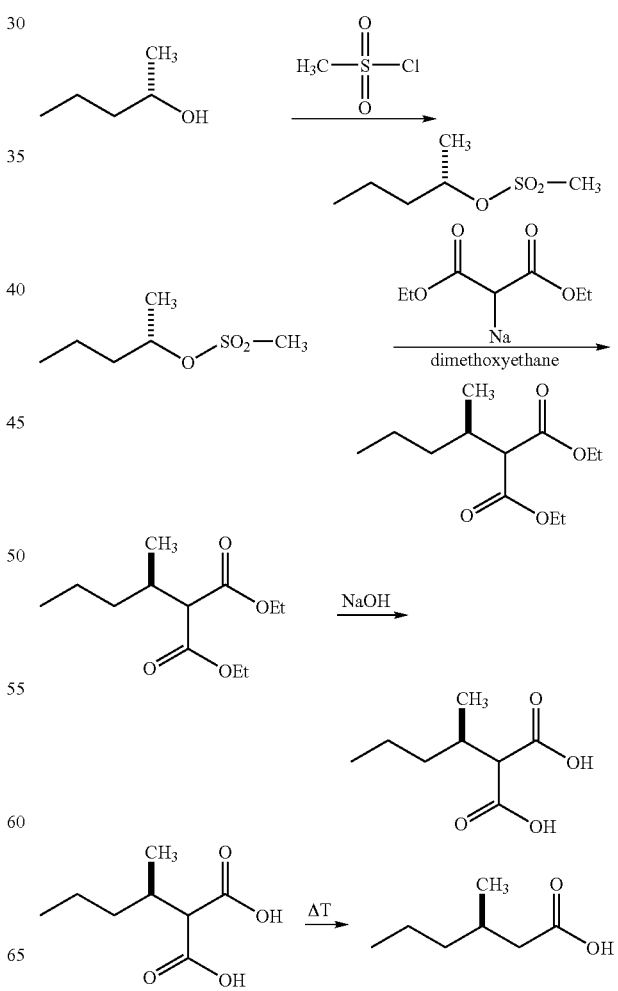

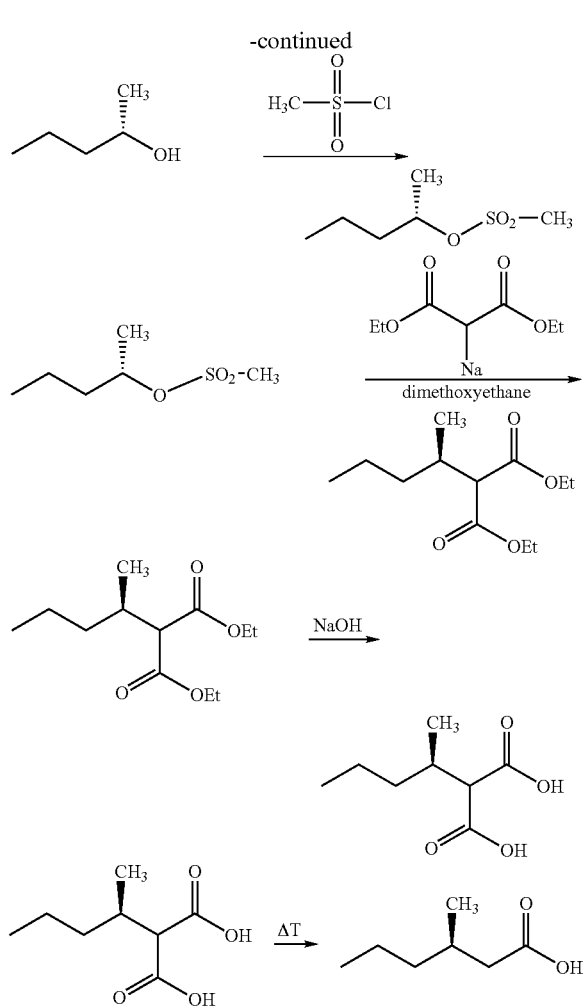

Possible embodiments of the $C_1$-$C_{15}$ hydrocarbon radicals $R^1$, $R^2$ and $R^3$ are linear or branched, cyclic or cyclic group-containing, saturated or unsaturated $C_1$-$C_{15}$-alkyl, $C_2$-$C_{15}$-alkenyl or $C_2$-$C_{15}$-alkynyl radicals.

The $C_1$-$C_{15}$ hydrocarbon radicals for $R^1$ and $R^2$ may optionally additionally be substituted by Q where Q may be selected from the group comprising F, Cl, Br, I, CN, $NO_2$, OH, phthalimido, $C_1$-$C_{10}$-alkoxy, $C_1$-$C_6$-trialkylsilyl, $C_1$-$C_6$-trialkylsilyloxy, $NH_2$, $C_1$-$C_{10}$-alkylamino, $C_1$-$C_6$-trialkylsilylamino, $C_1$-$C_6$-trialkylsilyl-$C_1$-$C_{10}$-alkyl-amino, aralkyloxy, N-(aralkyl)amino, N,N-(diaralkyl)-amino, aryl, aralkyl, alkaryl, aralkenyl, alkenylaryl or heteroaryl radicals, where the latter themselves may be substituted by radicals selected from the group of F, Cl, Br, I, CN, $NO_2$, $C_1$-$C_{10}$-alkoxy radicals, $C_1$-$C_{10}$-alkylamino radicals or $C_1$-$C_{10}$-alkyl radicals.

Particularly preferred radicals for $R^1$, $R^2$ and $R^3$, and also for R, are each independently methyl, ethyl, n-propyl, isopropyl, n-butyl, sec-butyl, tert-butyl, n-pentyl, n-hexyl, n-heptyl, cyclopropyl, cyclobutyl, cyclopentyl, cyclohexyl, allyl, vinyl, benzyl, benzyloxymethyl, benzyloxyethyl, benzyloxypropyl, -(benzylamino)methyl, -(benzylamino)ethyl, N,N-(dibenzylamino)methyl, N,N-(dibenzylamino)ethyl, phthalimidomethyl or phthalimidoethyl.

Particularly preferred substituents Q are fluorine, chlorine, bromine, nitro, cyano, hydroxyl, amino, N-methylamino, N,N-dimethylamino, N-benzyl, N,N-dibenzyl, phthalimido, N-acetylamino, N-acetyl-N-methylamino, N-benzyloxycarbonylamino, methoxy, ethoxy, phenoxy, benzyloxy, acetyl, propionyl, phenyl, naphthyl, benzyl, furyl, piperidinyl, pyrrolidinyl, quinolinyl, pyridyl, piperazinyl, imidazolyl, pirimidinyl, oxazolyl, isoxazolyl, morpholinyl, thiazolyl, isothiazolyl, indolyl, triazinyl, thienyl or thiophenyl, which may in turn be substituted by radicals selected from the group comprising methyl, ethyl, n-propyl, isopropyl, butyl, sec-butyl, tert-butyl, cyclopropyl, cyclobutyl, cyclopentyl, cyclohexyl, allyl, vinyl, phenyl, furyl, piperidinyl, pyrrolidinyl, quinolinyl, pyridyl, piperazinyl, imidazolyl, pirimidinyl, oxazolyl, isoxazolyl, morpholinyl, thiazolyl, isothiazolyl, indolyl, triazinyl, thienyl, thiophenyl, fluorine, chlorine, bromine, nitro, cyano, amino, hydroxyl, methoxy, ethoxy, phenoxy, trimethylsilyl, triethylsilyl, acetyl, propionyl, amino, N,N-dimethylamino, N-benzyl, N-acetylamino, N-acetyl-N-methylamino or N-benzyloxycarbonylamino, and also acetyl-, amino-, N-methylamino-, N,N-dimethyl-amino-, N-benzyl-, N-acetylamino-, N-acetyl-N-methyl-amino, N-benzyloxycarbonylamino-, nitro-, methyl-, ethyl-, propyl-, isopropyl-, butyl-, sec-butyl-, tert-butyl-, methoxy-, ethoxy-, phenoxy-, acetoxy-, benzyloxy-, trimethylsilyl-, trimethylsilyloxy-, triethylsilyloxy-, fluoro-, chloro-, bromo-, iodo- and cyanophenyl or -naphthyl.

The optically active alcohols (reactants), especially those of the general formula (IIa) or (IIb), are commercially available in enantiomerically pure or enantiomerically enriched form and can be obtained in enantiomerically pure form in an economically viable manner and on the industrial scale in particular by enantioselective reduction of the corresponding prochiral ketones in the presence of enzyme catalysts (T. C. Rosen, T. Daussmann, J. Stohrer, Chem. Spec., 2004, April, p. 39).

Alcohols prepared by biocatalytic reduction, especially those of the general formula (IIa) or (IIb), may comprise the corresponding prochiral ketone used for their preparation as an impurity. It has been found, surprisingly, that this ketone in no way adversely affects the preparation of the activated compounds by introducing a leaving group, particularly in the case of those activated compounds of the general formula (IIIa) or (IIIb), especially in the case of sulfonic esters. Instead, the ketone functions as a cosolvent and does not form any undesired by-products or impurities. On completion of conversion of the alcohols to the activated compounds, especially sulfonic esters, in step A), the ketones can be removed without any problem by distillation, crystallization or extraction.

The use of alcohols slightly contaminated with ketone as reactants without preceding purification makes the process particularly economically viable, so that, in a particularly preferred embodiment of the process according to the invention, it is possible to use alcohols contaminated with ketone, especially the ketone corresponding to the alcohol used. In particular, alcohols are used which, as direct process products, stem from a biocatalytic preparation process for enantiomerically pure or enantiomerically enriched secondary alcohols, especially from the process known in the prior art and cited above.

In step A), the alcohols, especially those of the general formula (IIa) or (IIb), are converted, with retention of configuration, to activated compounds, especially those of the general formula (IIIa) or (IIIb), by introducing a leaving group. Methods for activating alcohols as substrates for nucleophilic substitution are well known to those skilled in the art.

In these activated compounds, especially those of the general formula (IIIa) or (IIIb), the leaving group (X), in general, is selected from the group comprising halogen, sulfonic esters $OSO_2R$, sulfuric esters $OSO_2OR$ and carboxylic esters OCOR. In the activated compounds, especially those of the general formula (IIIa) or (IIIb), X is preferably a halide selected from chlorine, bromine or iodine, or sulfonic esters $OSO_2R$ where R here is preferably selected from fluorine, $C_1$-$C_{15}$-alkyl or $C_1$-$C_{20}$-aryl radicals, where the latter may in turn optionally be substituted by halogen, nitro or $C_1$-$C_{15}$-alkyl radicals. In the case of $C_1$-$C_{15}$-alkyl radicals for R, R may be selected from the particularly preferred embodiments of R mentioned above.

Particularly preferred leaving groups in the activated compounds, or X radicals, are sulfonic esters $OSO_2R$, among which preference is given particularly to those in which R is methyl, trifluoromethyl, phenyl or 4-methylphenyl, especially methyl or 4-methylphenyl.

The introduction of a sulfonic ester leaving group or of the X radicals (when they are $OSO_2R$) onto the alcohols to obtain the activated compounds, especially those of the general formula (IIIa) or (IIIb), is effected generally by reacting the alcohols with sulfonyl chlorides, especially in the presence of a base, as disclosed, for example, by R. W. Bates, T. R. Devi, Tetrahedron Lett., 1995, 36, p. 509.

The sulfonyl chlorides used are preferably methanesulfonyl chloride, trifluoromethanesulfonyl chloride, benzenesulfonyl chloride and toluenesulfonyl chloride, especially methanesulfonyl chloride and toluenesulfonyl chloride.

The bases used are in particular amine bases, more preferably triethylamine and pyridine.

The reaction is performed in inert solvents, for example methylene chloride, diethyl ether, tert-butyl methyl ether or toluene.

The temperature in the reaction in step A) is typically from −50 to +50° C., especially from −20 to +30° C.

It has been found to be useful to react the alcohol of the general formula, especially those of the general formula (IIa) or (IIb), with the sulfonyl chloride and optionally the amine in a molar ratio of 1:(1 to 2):(1 to 4), in particular 1:(1 to 1.3):(1 to 1.7).

The activated compounds prepared, especially the sulfonic esters, are processed further directly after the workup, especially by hydrolysis. It is also possible to purify them by distillation or crystallization before the further reaction in an additional step.

In step B), the activated compounds obtained in step A), especially those of the general formula (IIIa) or (IIIb), are reacted with a malonic acid derivative to give alkylated malonic acid compounds, especially those compounds of the general formula (IVa) or (IVb), with completely stereoselective inversion of configuration.

It has been found that, surprisingly, the preparation of the alkylated malonic acid compounds, especially those of the general formula (IVa) or (IVb)—contrary to the prevalent opinion in the prior art—proceeds with completely stereoselective inversion of configuration without racemization at the stereocenter with very high optical yields of >99% and simultaneously very high chemical yields of up to >90% when the alkylation is performed in one or more solvents selected from the class of the ethers or carboxylic esters, one or more aprotic polar solvents or alcohols optionally being added as a cosolvent, this addition being a maximum of 30% of the total volume of solvent added.

The proportion of the polar aprotic solvents added as cosolvents, based on the sum of the volumes of the solvents added overall, is preferably less than 25%, in particular less than 20%.

In a particular preferred embodiment of the reaction in step B), the reaction is performed exclusively in one or more of the solvents selected from the class of the ethers or carboxylic esters without further polar aprotic solvents or alcohols being added or present, especially in only a single solvent selected from the group of the ethers.

Ethers in the sense of the inventive step B) are generally those compounds that the person skilled in the art would include under this term, i.e. compounds which are characterized by a general structural element R—O—R, where R here is any organic radical. Ethers in the context of this invention are accordingly in particular simple or mixed dialkyl ethers, diaryl ethers, alkyl aryl ethers, cyclic ethers, geminal dialkoxy compounds (acetals), glycol ethers, polyethers and/or ethoxylates.

It is known that the substitution of malonic esters proceeds without racemization when the alkylation of the malonic ester is performed under mild reaction conditions, i.e. at low reaction temperature. In this case, strongly activating leaving groups, for example trifluoromethanesulfone or nitrobenzenesulfonate, are necessary. The use of trifluoromethanesulfonate as a leaving group for the alkylation of malonate at a temperature between 0° C. and room temperature is known, for example, from EP 684240. A disadvantage for the industrial use of these processes is that the sulfonyl halides or sulfonic anhydrides needed to prepare the activated sulfonic esters are very expensive, which makes these processes uneconomic for industrial use.

To avoid the expensive, strongly activating leaving groups, for example trifluoromethanesulfonate, processes have been proposed in which the cheaper but less activating leaving groups methanesulfonate or toluenesulfonate are used. Owing to the lower activating action of these sulfonates, the substitution reaction must, though, be performed at elevated reaction temperature in polar aprotic, activating solvents, for example dimethylformamide, dimethyl sulfoxide or hexamethylphosphoramide (HMPA). Under these reaction conditions, however, considerable racemization occurs. In addition, polar aprotic, activating solvents promote side reactions, which leads ultimately to poorer yields and lower purities of the products prepared.

For instance, T. Sato, J. Otera, J. Org. Chem., 1995, 60, p. 2627 disclose that the substitution of open-chain secondary methanesulfonates by the sodium salt of diethyl malonate in polar aprotic dimethylformamide as the solvent proceeds with considerable racemization. To avoid the racemization, Sato et al. propose a process in which the reaction of methanesulfonate with diethyl malonate in dimethylformamide is performed under non-basic, neutral conditions in the presence of cesium fluoride. For the methanesulfonate of (S)-2-octanol as the reactant, though, only yields of from 53 to 60% are achieved by this process. For this reason, and owing to the fact that an expensive auxiliary reagent in the form of cesium fluoride has to be used, this process is likewise of low suitability for industrial use.

It is also known from U. Berens, H.-D. Scharf, Synthesis, 1991, p. 832 that the reaction of the open-chain secondary toluenesulfonate of (S)-1-benzyloxypropan-2-ol with the potassium salt of di-tert-butyl malonate in dimethylformamide proceeds with partial racemization in an optical yield of 97% and only 65% chemical yield. For diethyl malonate, only a chemical yield of 44% was achieved in an analogous procedure. With dimethyl malonate, predominantly polymeric ester condensation products were obtained.

It is also known from M. Larcheveque, Y. Petit, Synthesis, 1991, p. 162 that the alkylation of di-tert-butyl malonate with toluenesulfonic or nitrobenzene-sulfonic esters of α-hydroxy esters in the tetrahydrofuran and hexamethylphosphoramide (HMPA) solvent mixture at room temperature proceeds in 80% yield with stereospecific inversion after 48 h. In order to achieve sufficient reactivity under these mild conditions, it is necessary to work in the presence of the strongly activating, polar aprotic solvent HMPA. However, only moderate chemical yields of from 61 to 80% were achieved. For the industrial use of this process, however, the long reaction times, the toxic properties of HMPA and the low yields of from only 60 to 80% should be mentioned as great disadvantages. This process too is therefore of low suitability for industrial use.

The process according to the invention is notable in particular that the addition of problematic HMPA as a cosolvent is dispensed with.

It is also known from J. Uenishi, M. Hamada, Chem. Pharm. Bull., 50, 2002, p. 697 that 1-(2-pyridinyl)ethyl methanesulfonate is substituted with inversion by malonic esters in a mixture of 6 parts of tetrahydrofuran and 4 parts of the activating polar aprotic solvent dimethyl sulfide. However, the yield of the reaction was only from 75 to 82%.

Moreover, J. M. Brown, J. E. MacIntyre, J. Chem. Soc., Perkin Trans II, 1985, p. 961 disclose the alkylation of the sodium salt of dimethyl malonate with 1-methyl-propyl (S)-toluenesulfonate in methanol as a solvent. The optical yield was not determined by Brown et al. However, the alkylation of malonate in the polar protic solvent methanol, and also in ethanol and isopropanol, proceeds with partial racemization (see Comparative Example 2).

When, in contrast, the reaction of the activated compounds, especially those containing a sulfonic ester leaving group, especially those of the general formula (IIIa) or (IIIb) where X is $OSO_2R$ where R is in particular methyl, phenyl or 4-methylphenyl, with malonic acid derivatives in step B) is performed in one or more solvents from the class of the ethers or carboxylic esters in the presence of polar aprotic solvents or alcohols, the proportion of the aprotic polar solvent(s) or alcohol(s) added not exceeding a proportion of 30% based on the sum of the volumes of the solvents used overall, the preparation of the alkylated malonic acid compounds, especially those of the general formula (IVa) or (IVb), proceeds, even at elevated temperature of 85° C., surprisingly with completely stereoselective inversion of configuration and without racemization with optical yields of >99%, and surprisingly also simultaneously very high chemical yields of up to >90% of theory with virtually full conversion. In addition, the stereospecific alkylation of the malonic acid compounds is surprisingly effected without noticeable formation of by-products with very high purity of the products prepared.

For example, the inventive reaction of enantiomerically pure 1-methylpentyl (S)-methanesulfonate of >99.9% ee with the sodium salt of diethyl malonate to form diethyl [(R)-1-methylpentyl]malonate in 1,2-dimethoxyethane proceeds completely stereospecifically without racemization with >99.9% ee and simultaneously very high chemical yield of 98% with a reaction time of only 5 h with very high space-time yield.

With the processes known from the prior art, the reaction, however, proceeds with a considerable degree of racemization and significantly poorer chemical yields of only from 44 to 82%.

Specifically, when the aforementioned reaction is performed in dimethylformamide as the solvent under the conditions described by U. Berens, H.-D. Scharf, Synthesis, 1991, p. 832, diethyl [(R)-1-methylpentyl]malonate is obtained not only with reduced chemical purity of <40% and a considerable proportion of impurities, but also with a significantly reduced enantiomeric excess of only 96.3% ee owing to partial racemization (see Comparative Example 1). In the solvents methanol, ethanol or isopropanol too, partial racemization takes place under otherwise identical conditions (see Comparative Examples 2).

This is all the more surprising in that—contrary to the prevalent opinion in the prior art—complete inversion at the stereocenter without racemization takes place even without addition of activating polar aprotic solvents or activating leaving groups in spite of high reaction temperatures of up to over 80° C. At the same time, the reaction products are prepared in a very economically viable manner in high chemical yields and in high purity with short reaction times. It is particularly surprising that the stereospecific alkylation in solvents from the class of the ethers or carboxylic esters, even in the presence of polar aprotic solvent or alcohol, the proportion of the polar aprotic solvent(s) added not exceeding a proportion of 30% based on the sum of the volumes of the solvents added overall, proceeds, even at temperatures of up to over 80° C., with very high purities compared to the prior art up to typically >90% and simultaneously very high purities of the products formed.

The reaction in step B) can generally be performed under acidic, neutral or basic conditions, preferably under basic conditions.

The malonic acid derivative is selected from the group comprising malonic acid, malonic monoesters, malonic diesters, preferably dialkyl malonates and bis(trialkylsilyl) malonates, especially dimethyl malonate and diethyl malonate.

The malonic acid derivative may be reacted either in the form of a salt deprotonated at least in the 2-position, or in the presence of a base.

The malonic acid derivatives used are preferably alkali metal salts of dialkyl malonate and bis(trialkylsilyl) malonate, especially the sodium or potassium salt of dimethyl malonate and diethyl malonate. It is also possible to use the alkali metal salt or alkaline earth metal salt of malonic acid or of a monoester. It is also possible to use mixed salts of malonic acid or of a monoester.

The alkali metal salts of the malonic esters are prepared by processes known to the person skilled in the art. In particular, the sodium or potassium salt of diethyl malonate or dimethyl malonate are prepared by initially charging a sodium or potassium base in a solvent and metering the malonic ester thereto, if appropriate dissolved in a solvent. It is also possible to add the sodium or potassium base, if appropriate dissolved in a solvent, to the malonic ester, if appropriate dissolved in a solvent. The sodium or potassium bases used may generally be sodium hydroxide, potassium hydroxide, sodium alkoxide, potassium alkoxide, sodium hydride or potassium hydride, especially sodium alkoxide, potassium alkoxide, sodium hydride and potassium hydride, more preferably sodium alkoxide and potassium alkoxide. The sodium or potassium alkoxides used are preferably sodium methoxide, potassium methoxide, sodium ethoxide, potassium ethoxide, sodium isopropoxide, potassium isopropoxide, sodium tert-butoxide or potassium tert-butoxide.

Suitable solvents for the preparation of the salts of the malonic acid derivatives are in particular alcohols and ethers. In a preferred embodiment of the process according to the invention, the salts are likewise prepared in the solvent from the class of the ethers selected for the reaction in step B). The reaction takes place at temperatures between –50 and 150° C., in particular between 10 and 80° C.

If appropriate, water or alcohol formed is distilled out of the reaction mixture. It is also possible to remove the reaction solvent by distillation after preparing the malonic salt and to replace it with another solvent, preferably from the class of the ethers.

To prepare the salt of the dialkyl malonate, it has been found to be useful to react the dialkyl malonate with the base, especially with the sodium or potassium base, in a molar ratio of (0.7 to 2):1. Preference is given to a molar ratio of (1 to 1.3):1.

Completion of preparation of the basic malonic acid alkali metal salt is followed by the reaction with the activated compound, especially those comprising sulfonic ester leaving groups or compounds of the general formula (IIIa) or (IIIb) in which X is $OSO_2R$ by combining the components, if appropriate dissolved in a solvent. To this end, the activated compound is added to the malonate salt or the malonate salt to the activated compound, if appropriate dissolved in each case in a solvent.

The solvents used in the inventive method for the stereospecific preparation of the alkylated malonic acid compounds, especially those of the general formula (IVa) or (IVb), which proceeds with complete inversion at the stereocenter, are solvents from the class of the ethers or carboxylic esters, if appropriate with an addition of polar aprotic solvent or alcohol of up to 30% based on the sum of the volumes of the solvents added overall.

In particular, for the reaction with the malonic acid derivative in step B), solvents selected from the group comprising cyclic ethers, especially tetrahydrofuran, 2-methyltetrahydrofuran, 2,5-dimethyltetrahydrofuran, 2,5-dimethoxytetrahydrofuran or 1,4-dioxane; open-chain di- and oligoethers having at least one ethylene bridge (glyme compounds), especially dimethoxyethane, diethoxyethane, diethylene glycol dimethyl ether, diethylene glycol diethyl ether, diethylene glycol dipropyl ether, diethylene glycol dibutyl ether, triethylene glycol dimethyl ether, triethylene glycol diethyl ether or triethylene glycol dibutyl ether, are preferred.

For the reaction with the malonic acid derivative in step B), preference is also given to solvents from the class of the carboxylic esters selected from the group comprising the methyl, ethyl, propyl, isopropyl, butyl, isobutyl, tert-butyl, pentyl, hexyl, benzyl esters of formic acid, acetic acid, propionic acid, butyric acid, valeric acid, especially the methyl, ethyl, propyl, isopropyl, butyl esters of acetic acid, propionic acid, butyric acid; particular preference is given here to ethyl acetate, propyl acetate, isopropyl acetate and/or butyl acetate.

The reaction may be performed in the presence of up to 30 parts by volume, based on the sum of the volumes of the solvents used overall, of polar aprotic solvent or alcohol as a cosolvent.

Suitable polar aprotic solvents are in principle all solvents of this type known to those skilled in the art. Polar aprotic solvents are characterized by a high solvation capacity for cations and/or anions, dielectric constants $\epsilon$ of from 20 to >100 and dipole moments $\mu$ of between 2.5 and 6 debye. The polar aprotic solvents used are especially nitriles, carboxamides, urea derivatives and sulfoxides, preferably acetonitrile, propionitrile, butyronitrile, formamide, N-methylformamide, dimethylformamide, diethylformamide, dimethylacetamide, diethylacetamide, N-methylpyrrolidone, 1,3-dimethyl-3,4,5,6-tetrahydro-2(1H)-pyrimidinone and dimethyl sulfoxide.

In the process according to the invention, there is explicitly no addition of hexamethylphosphoramide (HMPA) as a polar aprotic cosolvent.

In addition to polar aprotic solvents, alcohols are also suitable as cosolvents, especially methanol, ethanol, propanol, isopropanol, butanol, isobutanol, tert-butanol, pentanol, amyl alcohol; particular preference is given to methanol, ethanol and isopropanol.

In addition to aprotic solvents and alcohols, suitable cosolvents are in principle also amines, for example triethylamine, N,N,N',N'-tetramethylethylenediamine, pyridine, dimethylaniline, ketones, for example acetone, methyl ethyl ketone, and halogenated hydrocarbons, for example dichloroethane, trichloroethane, dichloropropane, trichloropropane, tetrachloromethane, or mixtures thereof.

It is also possible to use mixtures of two or more of the aforementioned solvents.

Particularly preferred solvents from the class of the ethers are selected from the group comprising tetrahydrofuran, 2-methyltetrahydrofuran, 2,5-dimethyltetrahydrofuran, 1,4-dioxane, dimethoxyethane, diethoxyethane, diethylene glycol dimethyl ether, diethylene glycol diethyl ether or triethylene glycol dimethyl ether. Particular preference is given to 1,4-dioxane, 1,2-dimethoxyethane, 1,2-diethoxyethane or diethylene glycol dimethyl ether.

Particularly preferred solvents from the class of the carboxylic esters are selected from the group comprising the methyl, ethyl, propyl, isopropyl or butyl esters of acetic acid, propionic acid or butyric acid. Particular preference is given to ethyl acetate, propyl acetate, isopropyl acetate and/or butyl acetate.

Particularly preferred polar aprotic cosolvents are acetonitrile, propionitrile, butyronitrile, formamide, dimethylformamide, dimethylacetamide and dimethyl sulfoxide.

In a particularly preferred embodiment, the proportion of the cosolvents added is less than 20% based on the sum of the volumes of the solvents added overall; in particular, the addition of a polar aprotic solvent or of an alcohol as a cosolvent is dispensed with entirely.

In a particularly preferred embodiment of the process according to the invention, step B) is performed exclusively in ethers, especially in only one ether, or exclusively in carboxylic esters, especially in only one carboxylic ester, the ethers and carboxylic esters each being selected from the aforementioned preferred embodiments of the solvent classes.

The reaction in step B) takes place at temperatures between 10 and 200° C., in particular between 40 and 140° C., more preferably between 60 and 100° C.

The reaction may also be performed in the presence of a phase transfer catalyst.

It has been found to be useful to react the malonic acid derivative with the activated compound, especially those of the class of the sulfonic esters, in a molar ratio of (0.7 to 2):1. Preference is given to a molar ratio of (1.0 to 1.3):1.

After the reaction has ended, it is possible first to remove and to recover a portion of the solvent by distillation, if appropriate under reduced pressure. After the reaction has ended, the reaction mixture is worked up, preferably by acidic aqueous or basic hydrolysis, if appropriate in the presence of a further solvent. The resulting product, especially one of the general formula (IVa) or (IVb), can optionally be purified in an additional step, by distillation, extraction or chromatography.

In a preferred embodiment of the process according to the invention, the crude product, which is already obtained in very pure form owing to the high achievable conversion, is processed further directly without further purification.

In step C), the alkylated malonic acid compounds obtained in step B), especially those of the general formula (IVa) or (IVb), are hydrolyzed to form the compounds of the corresponding acids, especially those of the general formula (Va) or (Vb), with full retention of the optical configuration.

When the malonic acid compound used is malonic acid itself, a salt of malonic acid or a silyl malonate, for example bis(trimethylsilyl)malonate, hydrolysis to the corresponding acids may be effected directly in step B) in the case of aqueous workup. In these cases, separate hydrolysis in step C) is not necessary.

When the malonic acid component used is a malonic ester, malonic monoester or a salt of these compounds, the ester is hydrolyzed in step C).

The alkylated malonic acid compounds, especially malonic esters of the general formula (IVa) or (IVb), again in particular dimethyl malonate and diethyl malonate, are hydrolyzed under aqueous and neutral, acidic or basic conditions, preferably under basic conditions by methods known to those skilled in the art.

For the hydrolysis under basic conditions, the alkylated malonic acid compounds obtained in step B) are optionally reacted with aqueous base in the presence of solvents. Suitable bases are all bases which are well known to those skilled in the art and are suitable for this purpose, especially alkali metal and alkaline earth metal hydroxide, alkali metal and alkaline earth metal oxide and alkali metal and alkaline earth metal alkoxide, preferably sodium hydroxide and potassium hydroxide.

The hydrolysis is effected at temperatures between 0 and 150° C., preferably 40 and 100° C.

The reaction can be performed monophasically, if appropriate in the presence of solvents, especially alcohol, preferably methanol and ethanol, or biphasically, if appropriate in the presence of solvents.

The hydrolysis is performed preferably in the presence of methanol and ethanol and directly by means of aqueous base without addition of further solvent. When no further solvent is used and the hydrolysis is performed in the alkaline aqueous medium, the reaction is particularly economically viable by virtue of achievement of high space-time yields.

Completion of hydrolysis is followed by workup and isolation of the products of the corresponding acids, especially those of the general formula (Va) or (Vb).

The workup is effected preferably by adding an acid and extracting with organic solvent. However, it is also possible to use other workup methods known to those skilled in the art.

The invention further provides the compounds of the general formula (Va) or (Vb)

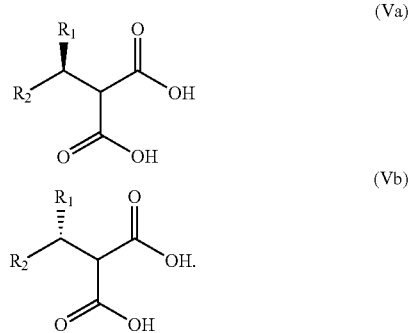

where $R^1$ and $R^2$ are each as defined above, especially selected from the abovementioned preferred embodiments.

The compounds of the general formula (Va) or (Vb) are obtainable in enantiomerically pure or enantiomerically enriched form as intermediates by means of the process according to the invention.

The compounds of the general formula (Va) or (Vb) are valuable synthesis intermediates of the process according to the invention, since they can be purified particularly efficiently in an optional additional step, and an increase in the chemical and optical yield (increase in the enantiomeric excess) of the desired end products thus becomes possible.

The invention therefore further provides a process for the enantiomeric enrichment of compounds of the general formulae (Va) or (Vb) by crystallization or recrystallization.

The compounds of the general formula (Va) or (Vb) are generally solids which can be purified easily by crystallization or recrystallization, which can improve the optical purity in particular. For example, it is possible for alcohols of the general formula (IIa) or (IIb) (reactants), which can be obtained only with a comparatively low optical purity of <95% ee, to improve the enantiomeric excess and the chemical purity in a controlled manner by crystallization in an optional additional step after step C). Thus, even reactants which are comparatively inexpensive because they are obtainable only in low optical purity can likewise be converted successfully by the process according to the invention without preceding additional and complicated enantiomeric enrichment.

For example, it has been found that, surprisingly, [(R)-1-methylbutyl]malonic acid and [(R)-1-methylpentyl]malonic acid can be enriched in one step from 95% ee to >99% ee in a high chemical yield of >90% by recrystallization from hexane as the solvent.

J. Cason, R. A. Coad, J. Am. Chem. Soc., 1950, 72, p. 4695 disclose that the preparation of [(S)-1-methylbutyl]malonic acid from (R)-2-pentanol by activation in the form (R)-2-bromopentane, alkylation of diethyl malonate with (R)-2-bromopentane in ethanol and hydrolysis of the diester to [(S)-1-methylbutyl]malonic acid proceeds with from 10 to 15% racemization. Owing to the excessively low optical purity of the [(S)-1-methylbutyl]malonic acid of 90% ee at best, it was not possible to perform an enantiomeric enrichment by crystallization, since the racemate crystallized preferentially. The process according to the invention now makes it possible for the first time to prepare the enantiomerically pure [(R)-1-methylbutyl]malonic acid starting from enantiomerically pure (S)-2-pentanol without racemization. It is also possible for the first time to enrich [(R)-1-methylbutyl]malonic acid from 95% ee to >99% ee by crystallization (analogously to Example 8). Owing to the high achievable enantiomeric excess of >95% ee, the enrichment by crystallization succeeds in a technically simple manner and in very high yield. Enantiomerically pure [(R)-1-methylbutyl]malonic acid is a valuable organic intermediate.

The invention accordingly further provides [(R)-1-methylbutyl]malonic acid which can be obtained as an intermediate by means of the process according to the invention.

The simple enantiomeric enrichment at the stage of the dicarboxylic acids of the general formula (Va) or (Vb) make the process according to the invention, for this reason too, particularly interesting and economically viable on the industrial scale.

In step D), the dicarboxylic acids obtained in step C), especially those of the general formula (Va) or (Vb), are decarboxylated with retention of configuration to give the desired process products (3-alkylcarboxylic acids), especially those of the general formula (Ia) or (Ib).

In some cases, full or partial decarboxylation to form the 3-alkylcarboxylic acids, especially those of the general formula (Ia) or (Ib), can occur actually in step C), especially in the case of acidic workup or elevated temperatures. In these cases, the step D), which otherwise has to be performed separately, is dispensed with.

The decarboxylation is performed under conditions known to those skilled in the art. The decarboxylation can be effected under neutral, acidic or basic conditions, preferably under neutral and acidic conditions.

The decarboxylation is effected more preferably in the form of a thermal decarboxylation at temperatures between 40 and 250° C., preferably between 80 and 180° C. For the thermal decarboxylation, the dicarboxylic acid, if appropriate in the presence of a solvent, is heated until full conversion. When the decarboxylation is performed in the presence of a solvent, the solvent can advantageously restrict the upper temperature range by virtue of its boiling point. Suitable solvents for the thermal decarboxylation are selected in particular from toluene, xylene or mesitylene.

On completion of reaction, the solvent is distilled off if appropriate and the product is isolated and, if appropriate, purified by distillation, crystallization or chromatography.

It is also possible to remove any organic impurities present from the 3-alkylcarboxylic acids, especially those of the general formula (Ia) or (Ib) or their corresponding salts, by extraction with an organic solvent in a basic medium.

For crystalline process products, especially those of the general formula (Ia) or (Ib), it is also possible to further increase the enantiomeric excess by crystallization or recrystallization.

The pressure range of all partial steps of the process according to the invention is uncritical and can be varied within wide limits. The pressure is typically from 0.01 to 20 bar; the process steps are preferably performed under standard pressure (atmospheric pressure).

The reaction is preferably performed with inertization with an inert protective gas, especially nitrogen or argon.

The reaction can be performed continuously or batchwise, preferably batchwise.

The advantages of the process according to the invention are in particular that the process enables the synthesis of the optically active 3-alkylcarboxylic acids starting from enantiomerically pure alcohols which are available inexpensively on the industrial scale, which are subjected in the course of the reaction to a complete stereoselective inversion, in simultaneously high chemical and optical yields, without the loss of stereochemical information of the chiral center which is known from the prior art occurring in the course of the synthesis as a result of racemization or partial racemization.

It is a particular advantage of the process according to the invention that, for the step of stereospecific substitution of the activated alcohol with malonic ester, very high yields of >90% are achieved with simultaneously very high chemical purities. The process enables the preparation of the desired products in very high space-time yields, which makes the process very attractive for industrial use.

The invention thus provides an alternative possible route to 3-alkylcarboxylic acids.

By virtue of the preparation of the optically active 3-alkylcarboxylic acids proceeding with very high chemical and optical yields using reactants and reagents available on the industrial scale, the process, in contrast to the processes known from the prior art, is particularly economically viable and is suitable in particular for industrial scale use.

The performance of the process is technically simple and very efficient overall. In contrast to the known processes, it also does not require any particular complicated process steps, for example a low-temperature reaction, or the use of particularly expensive assistants, for example butyllithium or cesium fluoride.

In addition, the process advantageously enables a technically simple and very efficient enrichment of the enantiomeric excess by crystallization at the stage of the dicarboxylic acids, especially those of the general formula (Va) or (Vb). This advantageously also allows secondary alcohols which are less expensive to obtain to be used as reactants with a relatively low optical purity. This makes the process particularly economically viable.

All symbols above in the formulae above are each defined independently of one another.

In the examples which follow, unless stated otherwise, all amounts and percentages are based on the weight, all pressures are 0.10 MPa (abs.) and all temperatures are 20° C. The examples serve to further illustrate the process according to the invention and should not be interpreted as a restriction in any way.

EXAMPLE 1

Preparation of (R)-3-methylheptanoic acid

1a: Preparation of 1-methylpentyl (S)-methanesulfonate

At room temperature, a three-neck flask with internal thermometer, dropping funnel and stirrer was initially charged under protective nitrogen gas with 54.9 g of (S)-2-hexanol (>99% ee, 0.537 mol) and 70.7 g of triethylamine (0.7 mol) in 550 ml of methylene chloride. 80 g of methanesulfonyl chloride (0.7 mol) were added undiluted at 0° C. to the mixture within 30 min, in the course of which a precipitate formed. Subsequently, the mixture was stirred at 0° C. for 60 min, hydrolyzed with 300 ml of saturated sodium hydrogencarbonate solution and stirred for 15 min. After phase separation, the mixture was washed with 300 ml of water and the organic phase was then dried over sodium sulfate. After solvent had been distilled off, 1-methylpentyl (S)-methanesulfonate was obtained in a yield of 96.6 g (99% of theory) and a chemical purity of 98% (GC).

1b: Preparation of diethyl [(R)-1-methylpentyl]malonate

At room temperature, a three-neck flask with internal thermometer, dropping funnel and stirrer was initially charged under protective nitrogen gas with 14.7 g of sodium hydride (95% pure, 0.583 mol) in 400 ml of dry 1,2-dimethoxyethane. Subsequently, 97.5 g of diethyl malonate (0.609 mol) were added dropwise at from 25 to 30° C. with evolution of hydrogen. The clear mixture was stirred at 25° C. for 30 min, and 93 g of 1-methylpentyl (S)-methanesulfonate (0.516 mol) were added undiluted. The mixture was heated to 85° C. and stirred for 5 h. After cooling to 25° C., the suspension was admixed with 600 ml of ether and 500 ml of saturated ammonium chloride solution. After phase separation, the organic phase was washed with 250 ml of water and then dried over sodium sulfate. After solvent had been distilled off, diethyl [(R)-1-methylpentyl]malonate was obtained in a yield of 123 g (98% of theory) and a chemical purity of 96% (GC).

1c: Preparation of [(R)-1-methylpentyl]malonic acid

At room temperature, 81 g of sodium hydroxide (2 mol) were dissolved in 360 ml of water and 160 ml of methanol in a three-neck flask with internal thermometer, dropping funnel and stirrer. 124 g of diethyl [(R)-1-methylpentyl]malonate (0.51 mol) were then added. The mixture was heated to 70° C. and stirred at this temperature for 3.5 h, in the course of which a solid formed. After cooling to 25° C., the suspension was admixed with 250 ml of ether and, with cooling, with 400 ml of 20% by weight hydrochloric acid. After phase separation, the aqueous phase was extracted twice with 100 ml of ether. The combined organic phases were washed with 100 ml of water and then dried over sodium sulfate. After solvent had been distilled off, [(R)-1-methylpentyl]malonic acid was obtained in a yield of 85 g (89% of theory) (m.p.: 123° C.).

1d: Preparation of (R)-3-methylheptanoic acid

At room temperature, 60 g of [(R)-1-methylpentyl]-malonic acid (0.318 mol) were dissolved in 120 ml of xylene in a three-neck flask with internal thermometer, condenser and stirrer. The mixture was heated to 125° C. for 5 h. After cooling to 25° C., the mixture was admixed with 200 ml of 2N sodium hydroxide solution. After phase separation, the aqueous phase was admixed with 200 ml of ether and, with cooling, with 180 ml of 15% by weight hydrochloric acid. After phase separation, the aqueous phase was extracted twice with 100 ml of ether. The combined organic phases were washed with 50 ml of water and then dried over sodium sulfate. After solvent had been distilled off, (R)-3-methylheptanoic acid was distilled and obtained in a yield of 35.5 g (77% of theory) with >99% ee and >99% chemical purity (b.p.: 67-68° C. at 0.45 mbar).

The entire synthesis sequence 1 a to 1 d proceeds without racemization.

EXAMPLE 2

Preparation of (R)-3-methylheptanoic acid

Analogously to Example 1, (R)-3-methylheptanoic acid was obtained in 65% of theory over all four stages starting from (S)-2-hexanol (>99% ee) which contained 20 mol % of 2-hexanone as the corresponding prochiral ketone (reactant for the biocatalytic reduction). It was possible to remove 2-hexanone without any problem by distillation at the stage of (S)-1-methylpentyl methanesulfonate.

EXAMPLE 3

Preparation of (R)-3-methylheptanoic acid

Analogously to Example 1, (R)-3-methylheptanoic acid was obtained in 67 and 69% of theory over all four stages when the preparation of diethyl [(R)-1-methylpentyl]malonate was performed in diethylene glycol dimethyl ether and 1,2-diethoxyethane as the solvent.

EXAMPLE 4

Preparation of (R)-3-methylhexanoic acid

4a: Preparation of (S)-1-methylbutyl methanesulfonate

Analogously to Example 1 a, 22.8 g (0.26 mol) of (S)-2-pentanol (98.4% ee) were used to obtain (S)-1-methylbutyl methanesulfonate in a yield of 42.1 g (98% of theory) and a chemical purity of 97% (GC).

4b: Preparation of diethyl [(R)-1-methylbutyl]malonate

Analogously to Example 1 b, 42.1 g (0.253 mol) of (S)-1-methylbutyl methanesulfonate were used to obtain Diethyl [(R)-1-methylbutyl]malonate in a yield of 56.5 g (97% of theory) and a chemical purity of 96% (GC).

4c: Preparation of [(R)-1-methylbutyl]malonic acid

Analogously to Example 1 c, 56.5 g (0.245 mol) of Diethyl [(R)-1-methylbutyl]malonate were used to obtain [(R)-1-methylbutyl]malonic acid in a yield of 40.5 g (95% of theory) (m.p.: 95° C.).

4d: Preparation of (R)-3-methylhexanoic acid

Analogously to Example 1 d, 40.5 g (0.232 mol) of [(R)-1-methylbutyl]malonic acid were used to obtain (R)-3-methylhexanoic acid in a yield of 25.5 g (84% of theory) with 98.4% ee and >99% chemical purity (b.p.: 81° C. at 2 mbar).

The entire synthesis sequence 4 a to 4 d proceeds without racemization.

EXAMPLE 5

Preparation of (R)-3-ethylheptanoic acid

Analogously to Example 1, (R)-3-ethylheptanoic acid was obtained starting from (S)-3-heptanol (>99% ee) in a yield of 66% of theory over all four stages with >99% ee and >99% chemical purity.

EXAMPLE 6

Preparation of (S)-5-benzyloxy-3-ethylpentanoic acid

Analogously to Example 1, (S)-5-benzyloxy-3-ethylpentanoic acid was obtained starting from (R)-1-benzyloxypentan-3-ol (>99% ee) in a purity of 61% of theory over all four stages with >99% ee and >99% chemical purity.

EXAMPLE 7

Preparation of (R)-3-methyl-5-phenylpentanoic acid

Analogously to Example 1, (R)-3-methyl-5-phenylpentanoic acid was obtained starting from (S)-4-phenylbutan-2-ol (>99% ee) in a yield of 63% of theory over all four stages with >99% ee and >99% chemical purity.

EXAMPLE 8

Recrystallization and Enrichment of [(R)-1-methylpentyl]malonic acid 24.8 g of [(R)-1-methylpentyl]malonic acid with 95% ee, prepared analogously to Example 1 starting from 2-hexanol with 95% ee, were dissolved in 120 ml of n-hexane at reflux. The clear solution was cooled to 18° C. within 6 h. The precipitate formed was filtered off and washed with 50 ml of cold n-hexane and dried under reduced pressure. 22 g of [(R)-1-methylpentyl]-malonic acid were obtained in a yield of 89% of theory with >99% ee.

EXAMPLE 9

Preparation of (R)-3-methylheptanoic acid

9a: Preparation of (S)-1-methylpentyl methanesulfonate

The preparation was effected analogously to Example 1a.

9b: Preparation of diethyl [(R)-1-methylpentyl]malonate

At room temperature, a three-neck flask with internal thermometer, dropping funnel and stirrer was initially charged under protective nitrogen gas with 14.7 g of sodium hydride (95% pure, 0.583 mol) in 290 ml of dry 1,2-dimethoxyethane and 50 ml of dry dimethylformamide. Subsequently, 97.5 g of diethyl malonate (0.609 mol) were added dropwise at from 25 to 30° C. with evolution of hydrogen. The clear mixture was stirred at 25° C. for 30 min and 93 g of (S)-1-methylpentyl methanesulfonate (0.516 mol) were added undiluted. The mixture was heated to 80° C. and stirred for 5 h. After cooling to 25° C., the suspension was admixed with 600 ml of ether and 500 ml of saturated ammonium chloride solution. After phase separation, the organic phase was washed with 250 ml of water and then dried over sodium sulfate. After distillative removal of solvent, diethyl [(R)-1-methylpentyl]malonate was obtained in a yield of 119 g (94% of theory) and a chemical purity of 95% (GC).

9c: Preparation of [(R)-1-methylpentyl]malonic acid

The preparation was effected analogously to Example 1c.

9d: Preparation of (R)-3-methylheptanoic acid

Analogous to Example 1 d. (R)-3-Methylheptanoic acid was obtained in a yield of 64% of theory over all stages with >99% ee and >99% chemical purity. Racemization was not observed in step 9 b.

EXAMPLE 10

Preparation of (R)-3-methylhexanoic acid

10a: Preparation of (S)-1-methylbutyl methanesulfonate

The preparation was effected analogously to Example 1a.

10b: Preparation of diethyl [(R)-1-methylbutyl]malonate

At room temperature, a three-neck flask with internal thermometer, dropping funnel and stirrer was initially charged under protective nitrogen gas with 41.8 g of sodium ethoxide (95% pure, 0.583 mol) in 250 ml of dry 1,2-dimethoxyethane and 30 ml of dry ethanol. Subsequently, 97.5 g of diethyl malonate (0.609 mol) were added dropwise at from 20 to 40° C., in the course of which a clear solution formed. The clear mixture was stirred at 40° C. for 30 min, and 85.7 g of (S)-1-methylbutyl methanesulfonate (0.516 mol) were added undiluted. The mixture was heated to 80° C. and stirred for 6 h. After cooling to 25° C., the suspension was admixed with 800 ml of methylene chloride and 500 ml of 5% by weight ammonium chloride solution. After phase separation, the organic phase was washed with 200 ml of water and then dried over sodium sulfate. After distillative removal of solvent, diethyl [(R)-1-methylbutyl]malonate was obtained in a yield of 113 g (95% of theory) and a chemical purity of 96% (GC).

10c: Preparation of [(R)-1-methylbutyl]malonic acid

The preparation was effected analogously to Example 1 c.

10d: Preparation of (R)-3-methylhexanoic acid

Analogous to Example 1 d. (R)-3-Methylhexanoic acid was obtained in a yield of 62% of theory over all stages with >99% ee and >99% chemical purity. Racemization was not observed in step 10 b.

EXAMPLE 11

Preparation of (R)-3-methylhexanoic acid

11a: Preparation of (S)-1-methylbutyl methanesulfonate

The preparation was effected analogously to Example 1 a.

11b: Preparation of diethyl [(R)-1-methylbutyl]malonate

At room temperature, a three-neck flask with internal thermometer, dropping funnel and stirrer was initially charged under protective nitrogen gas with 33.1 g of sodium methoxide (95% pure, 0.583 mol) in 250 ml of dry ethyl acetate. Subsequently, 97.5 g of diethyl malonate (0.609 mol) were added dropwise at from 20 to 30° C. The clear mixture was stirred at 25° C. for 30 min, and 85.7 g of (S)-1-methylbutyl methanesulfonate (0.516 mol) were added undiluted. The mixture was heated to 79° C. and stirred for 7 h. After cooling to 25° C., the suspension was admixed with 800 ml of methylene chloride and 500 ml of 5% by weight ammonium chloride solution. After phase separation, the organic phase was washed with 150 ml of water and then dried over sodium sulfate. After distillative removal of solvent, diethyl [(R)-1-methylbutyl]malonate was obtained in a yield of 105 g. The product contains dimethyl ester and ethyl methyl ester, formed by transesterification (GC purity: sum of Me/Me, Me/Et, Et/Et: 96%). The corrected yield is 96% of theory.

11c: Preparation of [(R)-1-methylbutyl]malonic acid

The preparation is effected analogously to Example 1 c.

11d: Preparation of (R)-3-methylhexanoic acid

Analogous to Example 1 d. (R)-3-Methylhexanoic acid was obtained in a yield of 62% of theory over all stages with 98.8% ee and >99% chemical purity (the optical purity has fallen from >99% ee to 98.8% ee).

COMPARATIVE EXAMPLE 1

Preparation of (R)-3-methylheptanoic acid(alkylation of malonate in dimethylformamide)

V1a: Preparation of (S)-1-methylpentyl methanesulfonate

The preparation was effected analogously to Example 1 a ((S)-2-hexanol: >99.9% ee).

V1b: Preparation of diethyl [(R)-1-methylpentyl]-malonate

At room temperature, a three-neck flask with internal thermometer, dropping funnel and stirrer was initially charged under protective nitrogen gas with 14.7 g of sodium hydride (95%, 0.583 mol) in 300 ml of dry dimethylformamide. Subsequently, 97.5 g of diethyl malonate (0.609 mol) were added dropwise at from 25 to 30° C. with evolution of hydrogen. The clear mixture was stirred at 25° C. for 30 min and 93 g of (S)-1-methylpentyl methanesulfonate (0.516 mol) were added undiluted. The mixture was heated to 85° C. and stirred for 5 h. After cooling to 25° C., the suspension was admixed with 1000 ml of methylene chloride and 600 ml of 5% by weight ammonium chloride solution. After phase separation, the organic phase was washed with 200 ml of water and then dried over sodium sulfate. After distillative removal of solvent, diethyl [(R)-1-methylpentyl]malonate was distilled (85° C., 0.6 mbar) and obtained in a yield of 48 g (38% of theory).

V1c: Preparation of [(R)-1-methylpentyl]malonic acid

The preparation is effected analogously to Example 1c.

V1d: Preparation of (R)-3-methylheptanoic acid

Analogous to Example 1d. (R)-3-Methylheptanoic acid was obtained in a yield of 26% of theory over all stages with 96.3% ee and 97% chemical purity (racemization).

COMPARATIVE EXAMPLE 2

Preparation of (R)-3-methylheptanoic acid(alkylation of malonate in alcohol)

V2a: Preparation of (S)-1-methylpentyl methanesulfonate

The preparation is effected analogously to Example 1 a ((S)-2-hexanol: >99.9% ee).

V2b: Preparation of dimethyl [(R)-1-methylpentyl]-malonate

At room temperature, 28.9 g of sodium methoxide (95% pure, 0.51 mol) were dissolved in 150 ml of dry methanol under protective nitrogen gas in a three-neck flask with internal thermometer, dropping funnel and stirrer. Subsequently, 85.3 g of diethyl malonate (0.533 mol) were added dropwise at from 30 to 35° C., in the course of which a suspension initially formed and dissolved toward the end of the addition. The clear mixture was stirred at 50° C. for 60 min and 80 g of (S)-1-methylpentyl methanesulfonate (0.444 mol) were added undiluted. The mixture was heated to 66° C. and stirred for 6 h. After cooling to 25° C., the suspension was admixed with 400 ml of methylene chloride and 300 ml of 5% by weight ammonium chloride solution. After phase separation, the organic phase was washed with 100 ml of water and then dried over sodium sulfate. After distillative removal of solvent, diethyl [(R)-1-methylpentyl]malonate was obtained in a yield of 94 g. The product comprises dimethyl ester and ethyl methyl ester, formed by transesterification, and unconverted malonic ester. The corrected yield is 84% of theory.

V2c: Preparation of [(R)-1-methylpentyl]malonic acid

The preparation is effected analogously to Example 1c.

V2d: Preparation of (R)-3-methylheptanoic acid

Analogous to Example 1d. (R)-3-Methylheptanoic acid was obtained in a yield of 56% of theory over all stages with 97.3% ee and 97% chemical purity (racemization).

Similar procedure with use of ethanol and isopropanol as solvents for the alkylation of malonate in V2b affords (R)-3-methylheptanoic acid with 97.4 and 98.0% ee (racemization).

The invention claimed is:

1. A process for preparing optically active 3-alkylcarboxylic acids, comprising the following steps:
   A) converting an optically active secondary alcohol to an optically active, activated compound by introducing a leaving group,
   B) reacting the activated compound with malonic acid or a malonic acid derivative to give an optically active, alkylated malonic acid compound, the reaction effected exclusively in the presence of one or more ether or carboxylic ester solvents and optionally one or more aprotic polar or alcohol solvents as a cosolvent in an amount of 30% or less of the total volume of solvent, with the proviso that the cosolvent is not hexamethylphosphoramide,
   C) if the product from step B) or a work-up thereof is not in the form of the acid corresponding to the malonic acid compound, hydrolyzing the malonic acid compound to the corresponding acid, and
   D) decarboxylating the corresponding acid.

2. The process of claim 1 wherein the optically active 3-alkylcarboxylic acid is one of the formula (Ia) or (Ib)

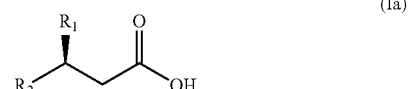

(Ia)

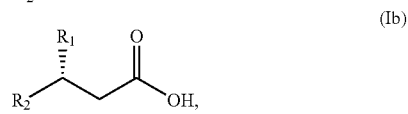

(Ib)

where $R^1$ and $R^2$ are each independently a linear or branched, saturated or unsaturated, cyclic or cyclic group-containing $C_1$-$C_{15}$ hydrocarbon radical which is optionally substituted by Q, wherein Q is selected from the group consisting of halogen, amino, amido, phthalimido, hydroxyl, cyano, nitro, alkoxy, aryloxy, aralkyloxy, alkylthio, acyl, silyl, silyloxy, aryl, and heteroaryl, comprising the steps:
   A) converting a compound of the formula (IIa) or (IIb)

(IIa)

-continued

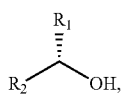
(IIb)

to an activated compound of the formula (IIIa) or (IIIb)

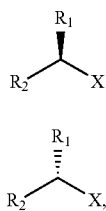
(IIIa)

(IIIb)

where

X is selected from the group comprising halogen, OSO$_2$R, OSO$_2$OR or OCOR and R is a linear or branched, saturated or unsaturated, cyclic or cyclic group-containing C$_1$-C$_{15}$ hydrocarbon radical which is optionally substituted by Q, or is fluorine, B) reacting the compound of the formula (IIIa) or (IIIb) obtained in step A) with a malonic acid derivative to obtain a compound of the formula (IVa) or (IVb),

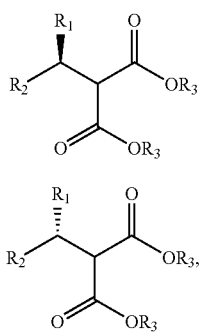
(IVa)

(IVb)

where

R$^3$ in the formula (IVa) or (IVb) are independently hydrogen or a linear or branched, saturated or unsaturated, cyclic or cyclic group-containing C$_1$-C$_{15}$ hydrocarbon radical, or are a C$_1$-C$_{20}$ trialkyl- or C$_1$-C$_{20}$ triarylsilyl radical, the reaction being effected exclusively in the presence of one or more ether or carboxylic ester solvents optionally containing one or more aprotic polar solvents or alcohol solvents as a cosolvent in an amount of not more than 30% of the total volume of solvent, and with the proviso that the cosolvent is not hexamethylphosphoramide, and C) if the product obtain from step (B) or a work-up thereof is not in the form of the acid corresponding to the malonic acid compound, hydrolyzing the compound of the formula (IVa) or (IVb) obtained in step B) to obtain a dicarboxylic acid of the formula (Va) or (Vb)

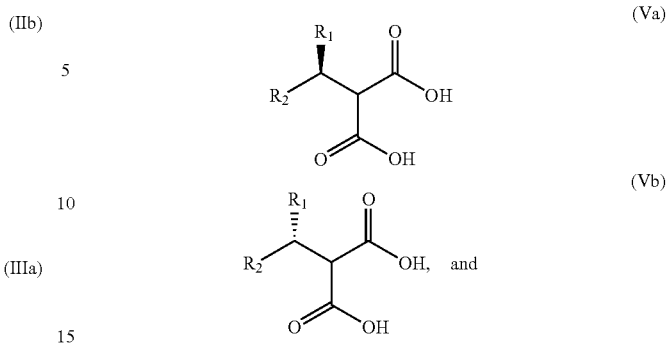

D) decarboxylating the dicarboxylic acid of the formula (Va) or (Vb). obtained in step C).

3. The process of claim 1, wherein in step B), at least one polar aprotic solvent selected from the group consisting of nitriles, carboxamides, urea derivatives and sulfoxides is employed.

4. The process of claim 2, wherein in step B), at least one polar aprotic solvent selected from the group consisting of nitriles, carboxamides, urea derivatives and sulfoxides is employed.

5. The process of claim 1, wherein in the reaction in step B), at least one polar aprotic solvent selected from the group consisting of acetonitrile, propionitrile, butyronitrile, formamide, N-methylformamide, dimethylformamide, diethylformamide, dimethylacetamide, diethylacetamide, N-methylpyrrolidone, 1,3 -dimethyl-3,4,5,6-tetrahydro-2(1H)-pyrimidinone and dimethyl sulfoxide is employed.

6. The process of claim 1, wherein in step B), at least one alcohol selected from the group consisting of methanol, ethanol, propanol, isopropanol, butanol, isobutanol, tert-butanol, pentanol and amyl alcohol is employed.

7. The process of claim 2, wherein in step B), at least one alcohol selected from the group consisting of methanol, ethanol, propanol, isopropanol, butanol, isobutanol, tert-butanol, pentanol and amyl alcohol is employed.

8. The process of claim 3, wherein in step B), at least one alcohol selected from the group consisting of methanol, ethanol, propanol, isopropanol, butanol, isobutanol, tert-butanol, pentanol and amyl alcohol is employed.

9. The process of claim 5, wherein in step B), at least one alcohol selected from the group consisting of methanol, ethanol, propanol, isopropanol, butanol, isobutanol, tert-butanol, pentanol and amyl alcohol is employed.

10. The process of claim 1, wherein cosolvent is present, and in a maximum of 20% of the total volume of solvent.

11. The process of claim 1, wherein the reaction in step B) is performed exclusively in the presence of one or more ether or carboxylic ester solvents.

12. The process of claim 1, the reaction in step B) is performed exclusively in the presence of one or more ether solvents.

13. The process of claim 2, the reaction in step B) is performed exclusively in the presence of one or more ether solvents.

14. The process of claim 1, wherein the compound(s) obtained in step C) are purified in an additional step before decarboxylation.

15. The process of claim 1, wherein step B) is performed in the presence of one or more solvents selected from the group consisting of tetrahydrofuran, 2-methyltetrahydrofuran, 2,5- dimethyltetrahydrofuran, 2,5-dimethoxytetrahydrofuran, 1,4-dioxane, dimethoxyethane, diethoxyethane, diethylene glycol dimethyl ether, diethylene glycol diethyl ether, diethylene glycol dipropyl ether, diethylene glycol dibutyl ether, triethylene glycol dimethyl ether, triethylene glycol diethyl ether and triethylene glycol dibutyl ether.

16. The process of claim 1, wherein step B) is performed exclusively in the presence of one or more solvents selected from the group consisting of tetrahydrofuran, 2-methyltetrahydrofuran, 2,5-dimethyltetrahydrofuran, 2,5-dimethoxytetrahydrofuran, 1,4-dioxane, dimethoxyethane, diethoxyethane, diethylene glycol dimethyl ether, diethylene glycol diethyl ether, diethylene glycol dipropyl ether, diethylene glycol dibutyl ether, triethylene glycol dimethyl ether, triethylene glycol diethyl ether and triethylene glycol dibutyl ether and ethyl acetate, propyl acetate, isopropyl acetate and butyl acetate.

17. The process of claim 2, wherein the compound(s) of the general formula (Va) or (Vb) are enantiomerically enriched by crystallization or recrystallization in an additional step.

* * * * *